the United States Patent (12) United States Patent
Saito et al.

(10) Patent No.: US 6,826,297 B2
(45) Date of Patent: Nov. 30, 2004

(54) DISPLAYING THREE-DIMENSIONAL MEDICAL IMAGES (75) Inventors: Motoaki Saito, Tokyo (JP); Kazuo Takahashi, Tokyo (JP); Keiji Ito, Tokyo (JP); Kimiaki Saito, Tokyo (JP)

(73) Assignee: TeraRecon, Inc., San Mateo, CA (US)

( * ) Notice: Subject to any disclaimer, the term of this patent is extended or adjusted under 35 U.S.C. 154(b) by 661 days.

(21) Appl. No.: 09/860,867

(22) Filed: May 18, 2001

(65) Prior Publication Data

US 2002/0172408 A1 Nov. 21, 2002

(51) Int. Cl.[7] .................................................. G06K 9/00
(52) U.S. Cl. ..................................... 382/131; 382/154
(58) Field of Search ................................ 382/128, 131, 382/132, 155, 154; 345/424, 653, 664, 679, 782; 378/4, 21; 600/425

(56) References Cited

U.S. PATENT DOCUMENTS

| | | | | |
|---|---|---|---|---|
| 5,381,518 A | * | 1/1995 | Drebin et al. ................ | 345/424 |
| 5,986,662 A | * | 11/1999 | Argiro et al. ................ | 345/424 |
| 6,480,732 B1 | * | 11/2002 | Tanaka et al. ............... | 600/425 |
| 6,664,961 B2 | * | 12/2003 | Ray et al. .................... | 345/424 |
| 2001/0031920 A1 | * | 10/2001 | Kaufman et al. ........... | 600/431 |

* cited by examiner

Primary Examiner—Andrew W. Johns
Assistant Examiner—Shervin Nakhjavan
(74) Attorney, Agent, or Firm—Blakely, Sokoloff, Taylor & Zafman LLP (57) ABSTRACT Multiple objects having the same physical property within a subject are displayed as distinct three-dimensional images in one or more views. Projection data obtained by scanning the subject with electromagnetic radiation are used to create a spatial distribution of absorption values for the subject that is displayed as an image on an image display unit. The spatial distribution is also stored as a series of voxels representing a three-dimensional image of the subject. Particular spatial regions within the image are defined as objects, with each object comprising a set of voxels. The objects are grouped into one or more views using a set selection panel on the image display unit. A density, gradient and color for each object in a view are determined based on properties input through the a series of object property setting panels on the image display unit. Each object in a particular view is associated with one of the property setting panels. A relationship between degrees of opacity and values for the voxels in an object is defined in the property setting panel for the object and used to determine the density. The density, gradient and color for the objects in a view are stored as a parameter set in memory and optionally, on a non-volatile medium for subsequent retrieval. A volume rendering process applies the data in the parameter sets to the stored voxels to create one or more views of the three-dimensional image. A viewpoint parameter provides a common viewpoint for displaying multiple views simultaneously in different areas of a display.

21 Claims, 4 Drawing Sheets

DISPLAYING THREE-DIMENSIONAL MEDICAL IMAGES

FIELD OF THE INVENTION

This invention relates generally to the displaying of three-dimensional medical image, and more particularly to displaying discrete images of objects having the same physical property.

COPYRIGHT NOTICE/PERMISSION

A portion of the disclosure of this patent document may contain material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. The following notice applies to the software and data as described below and in the drawings hereto: Copyright© 1999, TeraRecon Inc., All Rights Reserved.

BACKGROUND OF THE INVENTION

X-ray computerized axial tomography (CT) produces exact cross-sectional image data that express the physical property (electron density) of the human body. Reconstructions of three-dimensional images using multiple axial images acquired at different axial positions have been performed for some time. Helical-scan X-ray CT scanners and cone-beam X-ray CT scanners have been put to practical use recently. This has enabled more precise three-dimensional image reconstructions.

For three-dimensional display of medical images, a surface rendering method is often used that displays the interfaces between objects after extracting these interface planes from objects constituting a subject, and a volume rendering method is used that is based on a three-dimensional array of voxels having values relating to a physical property of the study subject.

In the case of the volume rendering method, anatomical regions of the subject are classified based on CT values in the three-dimensional array of the voxels that is constructed from X-ray CT slices. Therefore, one can separate spatial regions with different CT values as different objects. A spatial region with the same CT value is classified as one object, so one cannot separate a spatial region with this same CT value into different objects, even if the spatial region with this same CT value is separated geometrically. However, it is often desirable to separate a spatial region with the same CT value into two or more objects.

For example, one may want to remove the front portion of an organ to observe the inside of it so there is a need to separate the spatial region with the same CT value into two or more objects. For example, one may want to remove muscles of a front portion of extremities to observe relations of bones and muscles in these extremities so there is a need to separate the spatial region with the CT value for muscle into two or more objects.

For example, in a case of simulating joint motion, there is a need to separate a spatial region with the same CT value into two or more bones. For example, in the case of simulating a brain operation, there is a need to remove a small part of the skull with the same CT value as the rest of the skull, to open an aperture in the skull and observe inside.

When using the conventional volume rendering method, objects with different CT values can be separated from each other, but objects with same CT value cannot be separated into more than one object, even if the locations of the parts are different.

Volume rendering alone is therefore not suitable for an application that separates the spatial region with the same physical property into two or more objects, such as the simulation of an operation.

Additionally, the conventional volume rendering method requires a large amount of processing power, and reducing the processing time is very important. Therefore, because the processing time increases with the increase in the number of objects rendered, the amount of processing time required to handle a large number of objects means the conventional volume rendering method is often unsatisfactory for practical use.

Furthermore, the conventional volume rendering method permits objects with different physical properties to be separated from each other, but objects with the same physical property cannot be separated into more than one object, even if the locations of the parts are different.

There is a need to subdivide a spatial region with the same physical property into two or more objects while also reducing the processing time required to reconstruct the objects. Furthermore, there is a need to keep processing time at a minimal even if the number of objects is increased.

SUMMARY OF THE INVENTION

Multiple objects having the same physical property within a subject are displayed as distinct three-dimensional images in one or more views. Projection data obtained by scanning the subject with electromagnetic radiation are used to create a spatial distribution of absorption values for the subject that is displayed as an image on an image display unit. The spatial distribution is also stored as a series of voxels representing a three-dimensional image of the subject. Particular spatial regions within the image are defined as objects, with each object comprising a set of voxels. The objects are grouped into one or more views using a set selection panel on the image display unit. A density, gradient and color for each object in a view are determined based on properties input through the a series of object property setting panels on the image display unit. Each object in a particular view is associated with one of the property setting panels. A relationship between degrees of opacity and values for the voxels in an object is defined in the property setting panel for the object and used to determine the density. The density, gradient and color for the objects in a view are stored as a parameter set in memory and optionally, on a non-volatile medium for subsequent retrieval. A volume rendering process applies the data in the parameter sets to the stored voxels to create one or more views of the three-dimensional image. A viewpoint parameter provides a common viewpoint for displaying multiple views simultaneously in different areas of a display.

In another aspect of the invention, multiple sets of three-dimensional voxel data are acquired at different times or from different modalities. The parameter sets for one or more views having the same viewpoint are applied to the multiple sets of voxel data. The results can be displayed simultaneously in multiple areas of the display to enable comparisons of images of the objects at different times or with different types of apparatus.

Thus, a spatial region having a uniform physical property within a three-dimensional medical image can be subdivided into two or more objects that are displayed with different colors and opacities. When the number of objects increases, the volume rendering process can build the three-dimensional image quickly because all the necessary information is accumulated in the memory. Since volume rendering requires setting up a number of parameters, the invention can easily perform comparisons of a plurality of views of a three-dimensional image with different parameter settings by applying predefined object parameter-sets to the voxel values of the three-dimensional voxel data, thus eliminating the complicated and troublesome parameter setting process and more accurately reproducing the three-dimensional image.

Therefore, the invention can save processing power and produce a final image in a short processing time. Even if there are two or more objects, it is possible to display them on a single display screen, and it is possible to grasp the spatial relations of two or more objects correctly and easily. Furthermore, by grouping the objects constituting the subject into several views, the invention allows the display of a plurality of objects in multiple views with a common viewpoint.

In addition to the aspects and advantages of the present invention described in this summary, further aspects and advantages of the invention will become apparent by reference to the drawings and by reading the detailed description that follows.

DETAILED DESCRIPTION OF THE PREFERRED INVENTION

In the following detailed description of embodiments of the invention, reference is made to the accompanying drawings in which like references indicate similar elements, and in which is shown by way of illustration specific embodiments in which the invention may be practiced. These embodiments are described in sufficient detail to enable those skilled in the art to practice the invention, and it is to be understood that other embodiments may be utilized and that logical, mechanical, electrical, functional and other changes may be made without departing from the scope of the present invention. The following detailed description is, therefore, not to be taken in a limiting sense, and the scope of the present invention is defined only by the appended claims.

The following terms are used herein.

A "voxel" is a unit cube with a unit vector along the X-axis, a unit vector along the Y-axis, and a unit vector along the Z-axis of a three-dimensional image.

An "object" is an anatomical region of interest. An object is represented as a plurality of voxels having CT values in the range of specified CT values included in a spatial region specified for the object.

An "object parameter" is a parameter that specifies an object. It specifies the spatial region in which voxels constituting the object exist, and it includes the range of CT values of the voxels constituting the object. It also specifies opacity and color corresponding to the CT values of the voxels constituting the object.

An "object-set" is a plurality of objects included in a view of the three dimensional image.

An "object parameter-set" is a collection of object parameters for the objects included in a view of the three-dimensional image, i.e.; a collection of object parameters for a plurality of objects included in an object-set.

A set of "view data" is a data set of three-dimensional images of a plurality of objects. A set of view data of three-dimensional images of a subject is created by applying an object parameter-set to the voxel values of three-dimensional voxel data of a subject.

A "view" is a three-dimensional image of a plurality of objects. A view of a three-dimensional image of a subject is created by applying projection-process parameters to a set of view data of a three-dimensional image of a subject.

Figure 1:
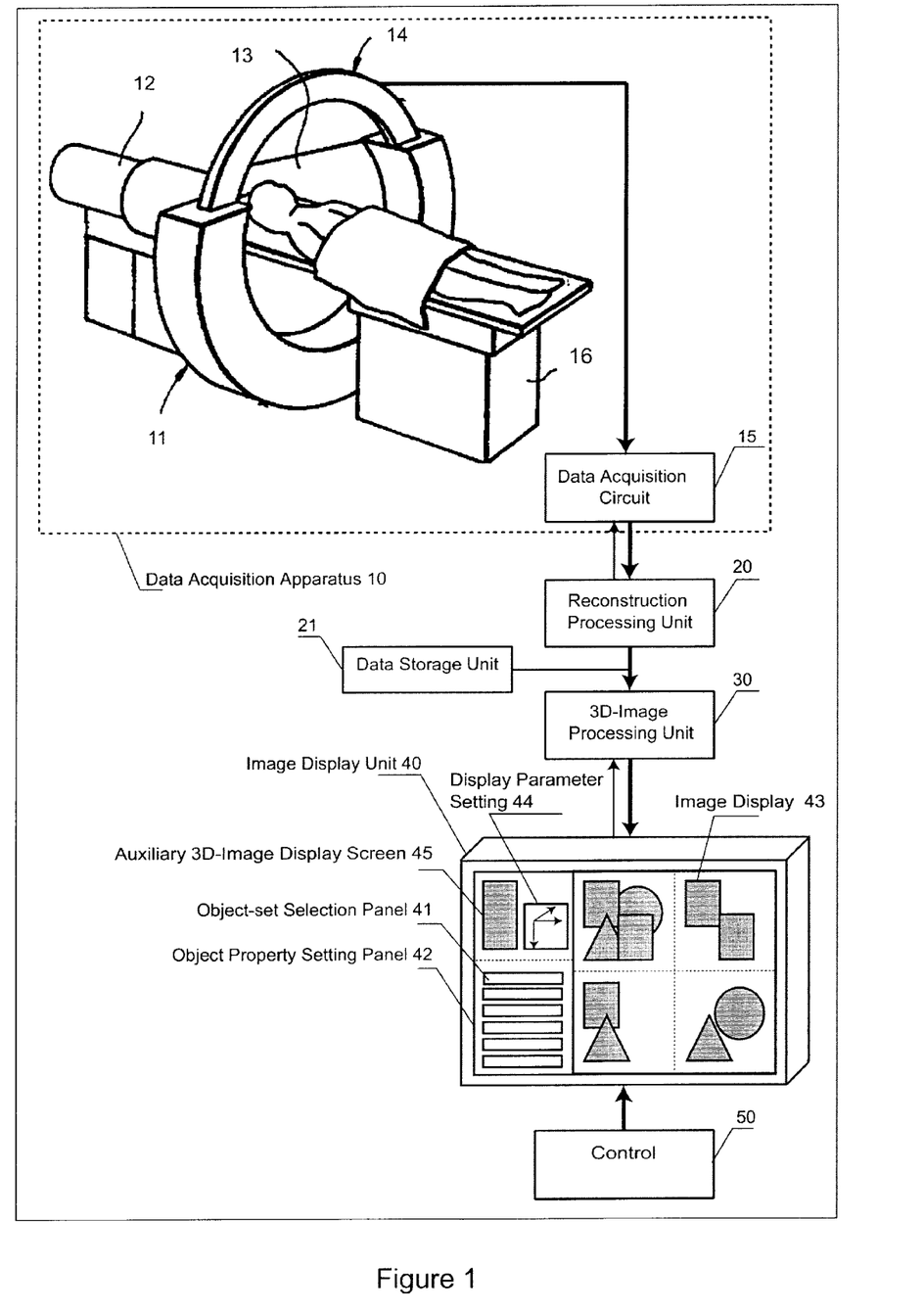
FIG. 1 is a schematic block diagram showing a configuration of the three-dimensional medical image display apparatus according to one embodiment of the present invention.

FIG. 1 is a block diagram showing one embodiment of this invention. A data acquisition apparatus 10 collects projection data of a subject by electro-magnetic radiation from the circumference and measures the transmitted dose. The data acquisition apparatus 10 is described herein as an X-ray computerized axial tomography (CT) scanner, such as an electron beam scanning type X-ray CT scanner, for purposes of explanation but the invention functions similarly in other apparatus such as a magnetic resonance (MR) or ultrasound apparatus and is not limited to use with X-ray CT scanners.

The apparatus 10 controls an electron beam 13 emitted from an electron gun 12 for scanning an X-ray target 11 annularly located around a subject. The X-ray beam generated by the X-ray target transmits the cross section of the subject on a bed 16, and an X-ray detector 14 intercepts the transmitted X-ray beam. A data acquisition circuit 15 converts output current of the X ray detector into digital data. By moving the bed 16, the apparatus 10 repeats the electronic beam scan, and collects projection data of two or more cross sections of the subject.

A reconstruction-processing unit 20 performs pre-processing, reconstruction processing, and post-processing of the acquired projection data, and creates an image that expresses a spatial distribution of CT values equivalent to the X-ray absorption coefficient of the subject. The reconstruction-processing unit 20 is a data-processing unit containing a processor programmed to reconstruct the projection data into image data. A data storage unit 21 stores the image data reconstructed in the reconstruction-processing unit 20. While the projection data is described as being obtained by X-ray CT equipment, it will be apparent that data can be obtained from other medical image equipment, such as magnetic resonance (MR) or Ultrasound equipment.

A three-dimensional image-processing unit 30 is a data processing unit programmed to reconstruct a three-dimensional image from the image data. The three-dimensional image-processing unit 30 carries out the reconstruction of the three-dimensional image by volume rendering the image data from the reconstruction-processing unit 20 or the image data stored in the data storage unit 21.

An image display unit 40 has an object-set selection panel 41; an object property setting panel 42; a three-dimensional image display screen 43; a display-parameter setting panel 44; and an auxiliary three-dimensional image display screen 45.

The auxiliary three-dimensional image display screen 45 is used for defining spatial regions of objects. The three-dimensional image display screen 43 is used to display a three-dimensional image reconstructed by the three-dimensional image-processing unit 30. The display-parameter (projection-process parameter) setting panel 44 is used to select a common viewpoint when multiple views of the three-dimensional images are displayed simultaneously.

The object-set selection panel 41 is used to select an object-set or multiple object-sets from a plurality of object-sets to display as a view or multiple views of the three-dimensional images of a subject. To define the properties of each object included in the selected object-set, the object-property setting panel 42 has a plurality of object-setting units that includes: a panel for selecting the object for display; a panel to define a spatial region of the object using the auxiliary three-dimensional display screen; a panel to define a relation between opacity and pixel-value of the object; and a panel to assign color to the object.

Figure 2:
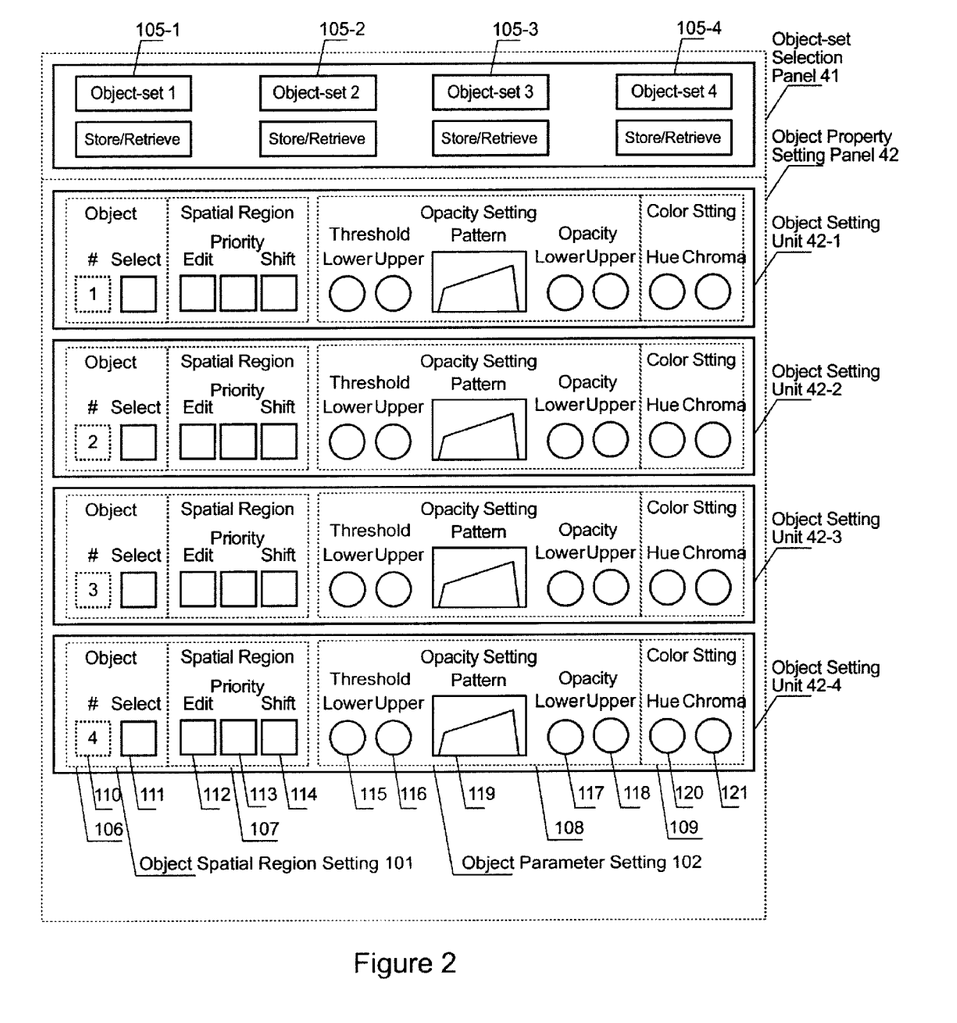
FIG. 2 is a drawing schematically showing a panel of the invention that selects an object-set from a plurality of object-sets of a subject and a panel that defines properties of each object included in the selected object-set.

FIG. 2 is a drawing of object-set selection panel 41 and the object-property setting panel 42. The object-set selection panel 41 has object-set selection switches 105-1, 105-2, 105-3, and 105-4 for selecting the object set. The number of object-set selection switches 105 is not limited to four.

After selecting an object-set by choosing one of the object-set selection switches 105-1, 105-2, 105-3, and 105-4, each of the object setting units 42-1, 42-2, 42-3, or 42-4 in the object property setting panel 42 is used to define the properties of one of the objects to be included in the selected object-set. The number of object setting units 42 are not limited to four. The object parameters for the objects in the object-set are stored as an object parameter-set. If the particular object parameter-set has been previously stored, the invention can retrieve the stored data set to set up the object parameters of the object-set.

Each of the object-setting units 42 has an object spatial-region setting section 101 and an object-parameter setting section 102. Each object spatial-region setting section 101 has an object selection panel 106 and an object spatial-region setting panel 107. Each object-parameter setting section 103 has an object-opacity setting panel 108 and an object-color setting panel 109.

Each object-selection panel 106 has a "number" display 110 that assigns a number to the object being defined in this object-setting unit. Each object-selection panel 106 has an "select" switch 111 that is used to include the object to reconstruct a three-dimensional image. By pushing the select switch 111, the object that is prepared in this object-setting unit is selected to participate in the reconstruction of a view of the three-dimensional image.

Each object spatial-region setting panel 107 has an "edit" switch 112, a "priority" switch 113, and a "shift" switch 114. The edit switch 112 is used to edit and define a spatial-region for the object using the three-dimensional image currently displayed on the auxiliary three-dimensional image display screen 45.

The priority switch 113 is used to set the priority order of the objects in relation with other objects for reconstructing three-dimensional images. The shift switch 114 is used to set an arbitrary spatial displacement of the object when reconstructing a three-dimensional image to shift the object's location on the display.

The object-opacity setting panel 108 has a "lower threshold" setting knob 115 and an "upper threshold" setting knob 116. The lower threshold setting knob 115 is used to define the lower limit of the CT values in the object that exists in the spatial-region defined by the object spatial-region setting panel 107. The upper threshold setting knob 116 is used to define the upper limit of the CT values in the object that exists in the spatial-region defined by the object spatial-region setting panel 107. An object consists of a set of voxels that exist in the spatial-region defined by the object spatial-region setting panel 107 and that have CT values between the lower threshold and the upper threshold.

The object-opacity setting panel 108 has an opacity "lower limit" setting knob 117 and an opacity "upper limit" setting knob 118. The opacity lower limit setting knob 117 is used to define the lower limit of the opacity values that are given to a set of voxels that have CT values between the lower threshold and the upper threshold. The opacity upper limit setting knob 118 is used to define the upper limit of the opacity values that are given to a set of voxels that have CT values between the lower threshold and the upper threshold.

A "pattern" panel 119 is used to define a function that expresses the relation between CT value and opacity value. The horizontal axis of the pattern panel 119 expresses CT value, and the vertical axis expresses the opacity value. By changing the curve of the pattern, the relation between opacity and CT value can be modified, within the lower limit and upper limit of opacity and within the lower threshold and upper threshold of CT value.

The object-color setting-panel 109 has a "hue" knob 120 and a "saturation" knob 121 (labeled "chroma" in FIG. 2). The hue knob 120 and the saturation knob 121 set color information for the object, i.e. the color of voxels that have CT values between lower threshold and upper threshold defined by switches 115 and 116, respectively, and exist in the spatial region defined in the object spatial-region setting part 101.

Using the object-setting unit 42-1, 42-2, 42-3, 42-4 etc., it is possible to set up the spatial region, range of CT values, range of opacities, and color information for each object of interest. Therefore it is possible to separate and display objects with the same physical property that exist in different spatial regions. This was difficult in the prior art of conventional volume rendering.

Figure 3:
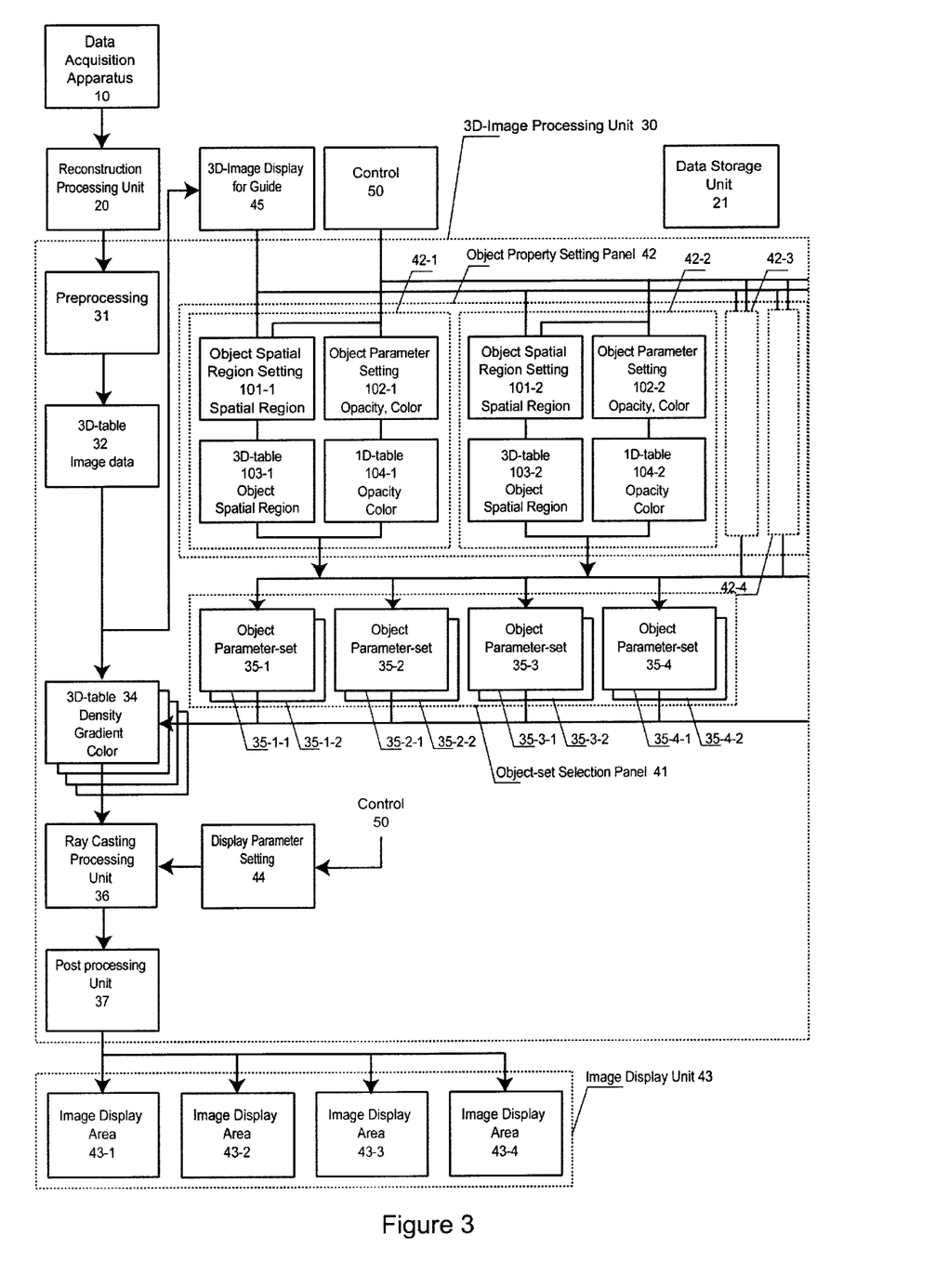
FIG. 3 is a block diagram of a three-dimensional medical image display apparatus according to the present invention.

FIG. 3 is a block diagram describing the operation of the embodiment of the invention in FIG. 1 in more detail. The data acquisition apparatus 10 collects projection data of two or more cross sections of a subject. The reconstruction-processing unit 20 creates image data of the cross sections by reconstruction processing of the projection data. The image data are transmitted to the three-dimensional image-processing unit 30. A pre-processing unit 31 performs image data processing on the transmitted image data, including compensation of an effect of gantry tilt of the X-ray CT apparatus and interpolation of image data in the direction of the body axis of a subject.

The interpolated image data is stored as voxels in the three-dimensional table 32 by the pre-processing unit 31. Image data for a first plane have an origin at the upper left corner; an X-axis that increases from left to right; and a Y axis intersecting perpendicularly with X-axis that increases top down. Image data for successive planes are stacked in the Z-direction that intersects perpendicularly with X-Y plane, in the order of the cross section positions in the subject. In the X-ray CT apparatus, the values in the three-dimensional table 32 are CT values.

The auxiliary three-dimensional image display screen 45 (labeled "3-D Image Display for Guide in FIG. 3) is used for specifying the spatial region of the object. The auxiliary three-dimensional image display screen 41 displays a three-dimensional image reconstructed from the voxel data stored in the three-dimensional table 32. Examples of such three-dimensional images are:

1) A multi-planer reformation image with an axial plane, a sagittal plane and a coronal plane;
2) an image made from stacking the cross sectional images; or
3) an image after three-dimensional processing.

One the object-set has been selected using the object-set selection panel 41, the object-property setting panel 42 is used to define objects through their properties as previously described. Each of the object-setting units 42-1, 42-2, 42-3, 42-4 is used to define the properties of one object of interest. In FIG. 3, only object-setting units 42-1 and 42-2 are illustrated for sake of simplicity. It will be appreciated that object-setting units 42-3 and 42-4 contain elements corresponding to those described below for object-setting units 42-1 and 42-2 and numbered accordingly. It will further appreciated that the invention is not limited to four object-setting units.

Using the three-dimensional image displayed on the auxiliary three-dimensional image display screen 45 and the object spatial-region setting panel 107 in the appropriate object-setting unit 42, the spatial-region of a particular object is defined as previously described. Each spatial region of the object defined in the object spatial-region setting panels 101-1, 101-2, 101-3, or 101-4 is mapped to a three-dimensional table 103-1, 103-2, 103-3, or 103-4. Each three-dimensional table 103-1, 103-2, 103-3, or 103-4 has the same three axes as the three-dimensional table 32. Within the spatial region for the reconstruction of the three-dimensional image, each voxel in table 103 has a value of 1. Outside of the spatial region for the reconstruction of the three-dimensional image, each voxel in table 103 has a value of 0.

As previously described, each object parameter setting panel 102-1, 102-2, 102-3, or 102-4 sets up the range of CT values, the degree of opacity and the color information for each object. This result is mapped to a one-dimensional table 104-1, 104-2, 104-3 or 104-4 in which the index is the CT value, and value 1 is the degree of opacity and value 2 is color information. Thus, each table 104 defines a relation between a CT value and a degree of opacity, and a relation between a CT value and color information. For each object in the range of CT values, the opacity, and the color is mapped according to the corresponding one-dimensional tables 104-1, 104-2, 104-3, or 104-4.

For example, the object parameter setting panel 102-1 defines the maximum and the minimum CT value that the object of interest has in the object spatial-region setting panel 101-1, the degree of opacity that each CT value within the range has, and the display color given to the object of interest. This result is mapped to the one-dimensional table 104-1.

For the range of CT values defined with the object parameter setting panel 102-1, 102-2, 102-3, or 102-4, the one-dimensional tables 104-1, 104-2, 104-3, or 104-4 contain the degrees of opacity corresponding to the CT values, and the color information assigned to the object. For example, each one-dimensional table 104-1, 104-2, 104-3, or 104-4 holds the degree of opacity and color information within the limits of CT values for each object of interest defined in the object-parameter setting panel 102-1, 102-2, 102-3, or 102-4, and outside of the range of CT values, the opacity is 0 and there is no color information.

Each of the object parameter-sets 35-1, 35-2, 35-3, or 35-4 contains the object parameters of all the objects included in the corresponding view of the three dimensional image. Object parameter-set 35-1 contains the data of the spatial regions defined in tables 103-1,103-2, 103-3, and 104-4 and the opacities and colors in 104-1,104-2, 104-3, and 104-4 for the plurality of objects included in object-set 1 that correspond to a first view of the three-dimensional image. Object parameter-set 35-2 contains the data of the spatial regions defined in tables 103-1, 103-2, 103-3, and 103-4 and the opacities and colors in 104-1,104-2, 104-3, and 104-4 of the plurality of objects included in object-set 2 that correspond to second view of the three dimensional image. Similarly, the data for third and fourth views are stored in subsequent object parameter-sets 35-3 and 35-4.

Each of the object parameter-sets 35-1, 35-2, 35-3 and 35-4 has a three-dimensional table 35-1-1, 35-2-1, 35-3-1, or 35-4-1 and a set 35-1-2, 35-2-2, 35-3-2, or 35-4-2 of four one-dimensional tables 35-1-2-1, 35-1-2-2, 35-1-2-3, 35-1-2-4, 35-2-2-1, 35-2-2-2, 35-2-2-3, 35-2-2-4, 35-3-2-1, 35-3-2-2, 35-3-2-3, 35-3-2-4, 35-4-2-1, 35-4-2-2, 35-4-2-3, or 35-4-24. The three-dimensional table of the object parameter-set 35-1-1, 35-2-1, 35-3-1, or 35-4-1 has same coordinates as the coordinates of the three-dimensional table 103-1, 103-2, 103-3, or 103-4. Each one-dimensional table 35-1-2-1, 35-1-2-2, 35-1-2-3, 35-1-2-4, 35-2-2-1, 35-2-2-2, 35-2-2-3, 35-2-2-4, 35-3-2-1, 35-3-2-2, 35-3-2-3, 35-3-2-4, 35-4-2-1, 35-4-2-2, 35-4-2-3, or 35-4-2-4 is same as one-dimensional tables 104-1, 104-2, 104-3, or 104-4. Thus, for the objects included in the object-set 1:

the spatial region of object 1 in three-dimensional table 103-1 is mapped on the value of three-dimensional table of the object parameter-set 1 35-1-1;

the spatial region of object 2 in three-dimensional table 103-2 is mapped on the value of three-dimensional table of the object parameter-set 1 35-1-1;

the spatial region of object 3 in three-dimensional table 103-3 is mapped on the value of three-dimensional table of the object parameter-set 1 35-1-1; and the spatial region of object 4 in three-dimensional table 103-4 is mapped on the value of three-dimensional table of the object parameter-set 1 35-1-1.

Each one-dimensional table 35-1-2-1, 35-1-2-2, 35-1-2-3, or 35-1-2-4 in a set 35-1-2 of one-dimensional tables contains the opacity and color information within the limits of the CT values defined in the object-parameter setting panels 102-1, 102-2, 102-3, or 102-4 for objects included in the object-set 1, and outside the limits of the CT values defined in the object-parameter setting panels 102-1, 102-2, 102-3, or 102-4, the opacity is equal to zero and there is no color information. Thus, for the objects included in the object-set 1:

the degree of opacity, and color information within the limits of CT values for object 1 in one-dimensional table 104-1 are mapped on the value of one-dimensional table of the object parameter-set 1 35-1-2-1;

the degree of opacity, and color information within the limits of CT values for object 2 in one-dimensional table 104-2 are mapped on the value of one-dimensional table of the object parameter-set 1 35-1-2-2;

the degree of opacity, and color information within the limits of CT values for object 3 in one-dimensional table 104-3 is mapped on the value of one-dimensional table of the object parameter-set 1 35-1-2-3; and the degree of opacity, and color information within the limits of CT values for object 4 in one-dimensional table 104-4 is mapped on the value of one-dimensional table of the object parameter-set 1 35-1-2-4.

A three-dimensional table 34 is a set of three-dimensional tables 34-1, 34-2, 34-3, and 34-4. Coordinates of each are same as the coordinates of the three-dimensional table 32. Each of the three-dimensional tables 34-1, 34-2, 34-3, or 34-4 contains the view data for object-set 1, object-set 2, object-set 3, or object-set 4 created by applying the corresponding object parameter-set 1 35-1, object parameter-set 2 35-2, object parameter-set 3 35-3, or object parameter-set 4 35-4 to the voxels in the three-dimensional table 32. Value 1 of each three-dimensional tables 34-1, 34-2, 34-3, or 34-4 is a density value, value 2 is a derivative (gradient) along the X-axis direction, Y-axis direction and Z-axis direction, and value 3 is a color value.

If a voxel in the three-dimensional table 32 exists in the spatial region defined in the object parameter-set 35-1-1, and it has CT values within the limits of CT values defined in the object parameter-set 35-1-2, the density value of the voxel of the three-dimensional table 34-1 is obtained by multiplying the CT value of the voxel in the three-dimensional table 32 with the opacity in the object parameter-set 35-1-2.

If a voxel in the three-dimensional table 32 exists in the spatial region defined in the object parameter-set 35-2-1, and it has CT value within the limits of CT value defined in the object parameter-set 35-2-2, the density value of the voxel of the three-dimensional table 34-2 is obtained by multiplying the CT value of the voxel in the three-dimensional table 32 with the opacity in the object parameter-set 35-2-2.

If a voxel in the three-dimensional table 32 exists in the spatial region defined in the three-dimensional table 35-3-1, and it has a CT value within the limits of CT value defined in the one-dimensional table 35-3-2, the color value of the voxel of the three-dimensional table 34-3 is the same as the color value of the object parameter-set 35-3-2.

If a voxel in the three-dimensional table 32 exists in the spatial region defined in the three-dimensional table 35-4-1, and it has a CT value within the limits of CT value defined in the one-dimensional table 35-4-2, the color value of the voxel of the three-dimensional table 34-4 is the same as the color value of the object parameter-set 35-4-2.

The derivative value is the gradient of the CT values that is calculated from the CT values of the voxels near the voxel in the three-dimensional table 32.

The ray-casting processing unit 36 calculates the pixel values projected onto a screen, using density data, derivative data, and color data that are accumulated in the three-dimensional table 34-1, 34-2, 34-3, or 34-4. The ray-casting processing unit 36 uses the same viewpoint for the projection-process of multiple sets of view data of multiple object sets, and creates multiple sets of views of three-dimensional images with the same viewpoint.

A post-processing unit 37 performs any necessary post-processing, for example, an affine conversion for geometry correction on data obtained in the ray-casting processing unit 36, and creates the image for display on the image display unit 43.

A series of typical operations to create a three-dimensional image is described next.

(1) Select object-set
 (1.1) Select object-set, for example object-set 1, using the object-set switch 105-1, 105-2, 105-3, or 105-4 in the object-set selection panel 41 (FIG. 2).
(2) Define Object
 (2.1) Define object 1, using the object-setting unit 42-1 of object property setting panel 42.
  (2.1.1) Operator selects switch 110 for object 1.
  (2.1.2) Selecting switch 112, the operator defines the spatial region of object 1.
  (2.1.3) Using knob 115 and knob 116, the operator defines the lower limit of the CT values and upper limit of the CT values of object 1.
  (2.1.4) Using knob 117 and knob 118, the operator defines the lower limit of the opacity values and upper limit of the opacity values of object 1.
  (2.1.5) If necessary, using pattern panel 119, the operator defines opacity curve of object 1.
  (2.1.6) Using knob 120 and knob 121, the operator defines hue and saturation of object 1.
  (2.1.7) If necessary, selecting switch 114, the operator expands or decreases the spatial region and shifts location of object 1.
 (2.2) Define object 2, using the object-setting unit 42-2
  (2.2.1) Operator selects switch 110 for object 2.
  (2.2.2) Selecting switch 112, the operator defines spatial region of the object 2.
  (2.2.3) Using knob 115 and knob 116, the operator defines the lower limit of the CT values and the upper limit of the CT values of object 2.
  (2.2.4) Using knob 117 and knob 118, the operator defines the lower limit of the opacity values and the upper limit of the opacity values of object 2.
  (2.2.5) If necessary, using pattern panel 119, the operator defines the opacity curve of object 2.
  (2.2.6) Using knob 120 and knob 121, the operator defines hue and saturation of object 2.
  (2.2.7) If necessary, selecting switch 114, the operator expands or decreases the spatial region and shifts the location of object 2.
 (2.3) Define object 3, using the object-setting unit 42-3.
  (2.3.1) Operator selects switch 110 for object 3.
  (2.3.2) Selecting switch 112, the operator defines the spatial region of the object 3.
  (2.3.3) Using knob 115 and knob 116, the operator defines the lower limit of the CT value and upper limit of the CT value of the object 3.
  (2.3.4) Using knob 117 and knob 118, the operator defines the lower limit of the opacity values and the upper limit of the opacity values of object 3.
  (2.3.5) If necessary, using pattern panel 119, the operator defines the opacity curve of object 3.
  (2.3.6) Using knob 120 and knob 121, the operator defines hue and saturation of object 3.
  (2.3.7) If necessary, selecting switch 114, the operator expands or decreases the spatial region and shifts the location of object 3.
 (2.4) Define object 4, using the object-setting unit 42-4.
  (2.4.1) Operator selects switch 110 for object 4.
  (2.4.2) Selecting switch 112, the operator defines the spatial region of the object 4.
  (2.4.3) Using knob 115 and knob 116, the operator defines the lower limit of the CT value and upper limit of the CT value of the object 4.
  (2.4.4) Using knob 117 and knob 118, the operator defines the lower limit of the opacity values and the upper limit of the opacity values of object 4.
  (2.4.5) If necessary, using pattern panel 119, the operator defines the opacity curve of object 4.
  (2.4.6) Using knob 120 and knob 121, the operator defines hue and saturation of object 4.
  (2.4.7) If necessary, selecting switch 114, the operator expands or decreases the spatial region and shifts the location of object 4.
(3) Select object for reconstruction, using the selection switch 111.
 (3.1) Press the selection switch 111 of the object-setting panel 42-1 to include object 1.
 (3.2) Press the selection switch 111 of the object-setting panel 42-2 to include object 2.
 (3.3) Press the selection switch 111 of the object-setting panel 42-3 to include object 3.
 (3.4) Press the selection switch 111 of the object-setting panel 42-4 to include object 4.
(4) Set the priority of the object, using the priority switch 112.
 (4.1) Set the priority switch 112 of the object setting panel 42-1 to "2" for object 1.
 (4.2) Set the priority switch 112 of the object setting panel 42-2 to "1" for object 2.
(5) Store object parameter-set
 (5.1) Store the object parameter-set 1 to the object parameter-set 35-1.
 (5.1) If necessary, go to section (1) and select another object-set, using one of the object-set switches 105-2, 105-3, and 105-4 in the object-set selection panel 41.
(6) Mapping density, gradient and color on the three-dimensional memory 34.
 (6.1) For the spatial region that has value of 1 in the three-dimensional table 35-1-1, the invention calculates density from the CT value in the three-dimensional table 32 and the opacity and CT value relation in the one-dimensional table 35-1-2 and maps it on the three-dimensional table 34-1 value 1, and calculates color from the CT value in the three-dimensional table 33 and the color and CT value relation in the one-dimensional memory 35-1-2 and maps it on the three-dimensional table 34-1 value 3.

(6.2) For the spatial region that has value of 1 in the three-dimensional table 35-2-1, the invention calculates density from the CT value in the three-dimensional table 32 and the opacity and CT value relation in the one-dimensional table 35-2-2 and maps it on the three-dimensional table 34-1 value 1, and calculates color from the CT value in the three-dimensional table 33 and the color and CT value relation in the one-dimensional memory 35-2-2 and maps it on the three-dimensional table 34-1 value 3.

(6.3) For the spatial region that has value of 1 in the three-dimensional table 35-3-1, the invention calculates density from the CT value in the three-dimensional table 32 and the opacity and CT value relation in the one-dimensional table 35-3-2 and maps it on the three-dimensional table 34-1 value 1, and calculates color from the CT value in the three-dimensional table 33 and the color and CT value relation in the one-dimensional memory 35-3-2 and maps it on the three-dimensional table 34-1 value 3.

(6.4) For the spatial region that has value of 1 in the three-dimensional table 35-4-1, the invention calculates density from the CT value in the three-dimensional table 32 and the opacity and CT value relation in the one-dimensional table 35-4-2 and maps it on the three-dimensional table 34-1 value 1, and calculates color from the CT value in the three-dimensional table 33 and the color and CT value relation in the one-dimensional memory 35-4-2 and maps it on the three-dimensional table 34-1 value 3.

(7) The ray-casting processing unit 36 calculates the pixel value projected on a screen, using density data and gradient data that are accumulated in the three-dimensional table 34-1 value-1 and value-2, the color information accumulated in the three-dimensional table 34-1 value-3, and the viewpoint setting 44.

(8) The post-processing unit 37 performs post-processing, for example, an affine conversion for geometry correction on data obtained in the ray-casting processing unit 36, and creates the image finally displayed on the image display unit 40.

(9) Store the object-parameter set-1.

If necessary, go to section (1) for next object-set.

(10) Retrieve one of the stored object-parameter sets, and reproduce previous view of the three-dimensional image.

When multiple object-sets are chosen, each view of the three-dimensional image is displayed in one of the multiple display areas 43-1, 43-2, 43-3, and 43-4 on the image display unit 40.

Even if there are a plurality of objects in an object-set, a single ray-casting process can build a view of the three-dimensional image quickly because all the information is accumulated in the three-dimensional table 34. Therefore, the invention can save processing power and produce a final image in a short processing time. Even if there are a plurality of objects, it is possible to display them on a single display screen, and it is possible to grasp the spatial relations of a plurality of objects correctly and easily.

Because a three-dimensional image that contains a plurality of classes of objects may be difficult to understand, the invention enables the grouping of objects by classes, and then creates several views of the three-dimensional image. Each view contains objects relating to a small number of classes, and corresponds to one object parameter-set. The invention then displays the multiple views of a three-dimensional image of a subject from a common viewpoint in multiple display areas on the same display. Even if all the objects in a subject are selected for view, it is possible to display the objects in an easy-to-see manner. Thus, an observer is able to grasp the spatial relations of many objects correctly and easily.

For example, assume two sets of images of a subject, one set taken before contrast-medium injection of the subject and one set taken after contrast-medium injection. In this case, there will be multiple data sets of three-dimensional voxels having values corresponding to the physical properties of the subject at the different times. The three-dimensional table 34 will thus contain multiple data sets, each of which is calculated by applying an object parameter-set to one of the data sets of the three-dimensional voxels. The ray casting processing unit 36 processes the multiple data sets 34 with the common view point parameter defined in the display parameter setting 44, and the resulting views are displayed in the image display areas 43-1, 43-2, 43-3, 43-4 on image display 43. Therefore it is possible to display time-series three-dimensional images with same view point on the image display unit 40, making it easy to observe the differences in the three-dimensional images.

In another example, assume two sets of images of a subject, one set acquired from a CT scanner and another set acquired from an MRI apparatus. In this case, there will be multiple data sets of three-dimensional voxels having values corresponding to the physical properties of the subject as measured with different modalities. As in the previous example, the three-dimensional table 34 contains multiple data sets, each of which is calculated by applying an object parameter-set to one of the data sets of the three-dimensional voxels. The ray casting processing unit 36 processes the multiple data sets 34 with the common view point parameter defined in the display parameter setting 44, and the resulting views are displayed in the image display areas 43-1, 43-2, 43-3, 43-4 on image display 43. Therefore, it is possible to display multi-modality three-dimensional images with the same view point on the image display unit 40, making it easy to compare the three-dimensional images from different apparatus.

Additionally, by changing a viewpoint location through the display parameter setting 44, it is possible to move the viewpoints of the multiple views at same time.

Furthermore, the invention speeds up the complicated time-consuming procedure of three-dimensional image display by storing and retrieving object parameter-sets containing various setup parameters of three-dimensional image display, which is a procedure. Thus, it is possible to reproduce a prior three-dimensional image display by retrieving prior object parameter-sets containing various setup parameters of three-dimensional image display, and it is possible to compare multiple three-dimensional image display procedures.

Figure 4:
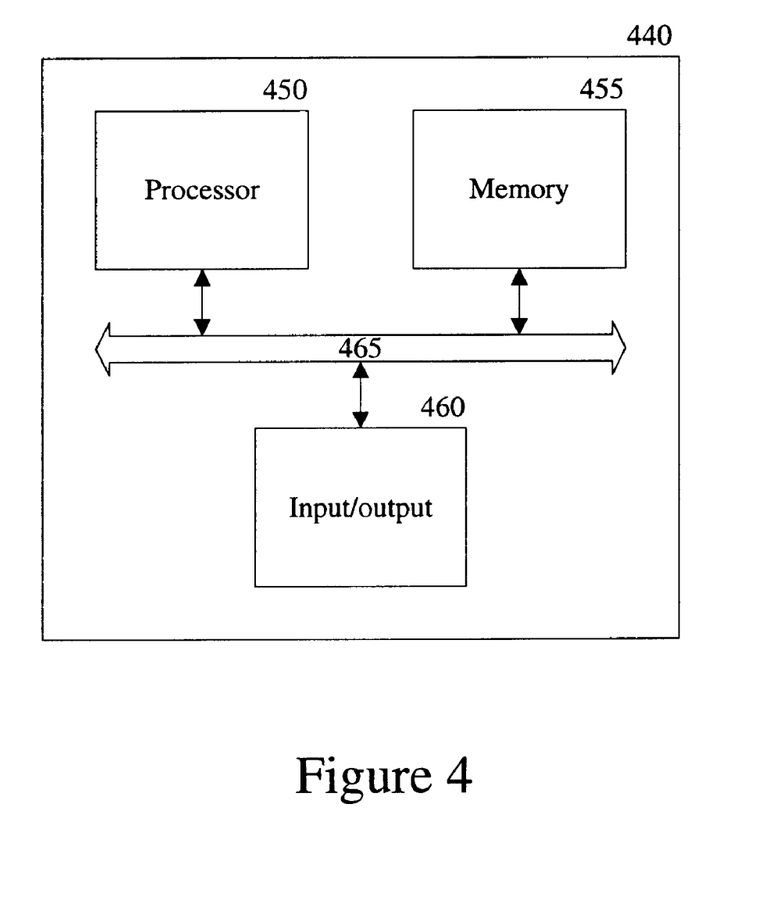
FIG. 4 is a block diagram of a data-processing unit suitable for use with the present invention.

Turning now to FIG. 4, one embodiment of a computer system 400 for use with the present invention is described. The system 400, includes a processor 450, memory 455 and input/output capability 460 coupled to a system bus 465. The memory 455 is configured to store instructions which, when executed by the processor 450, perform the functions of the invention described herein. The memory 455 may also store the various tables previously described and the results of the processing of the data within those tables. Input/output 460 provides for the delivery and display of the images or portions or representations thereof. Input/output 460 also provides for access to the image data provided by other components and for user control of the operation of the invention. Further, input/output 460 encompasses various types of computer-readable media, including any type of storage device that is accessible by the processor 450. One of skill in the art will immediately recognize that the term "computer-readable medium/media" further encompasses a carrier wave that encodes a data signal.

The computer-executable instructions may be written in a computer programming language or may be embodied in firmware logic. If written in a programming language conforming to a recognized standard, such instructions can be executed on a variety of hardware platforms and for interface to a variety of operating systems. In addition, the present invention is not described with reference to any particular programming language. It will be appreciated that a variety of programming languages may be used to implement the teachings of the invention as described herein. Furthermore, it is common in the art to speak of software, in one form or another (e.g., program, procedure, process, application, module, logic . . . ), as taking an action or causing a result. Such expressions are merely a shorthand way of saying that execution of the software by a computer causes the processor of the computer to perform an action or a produce a result.

The foregoing description of FIG. 4 is intended to provide an overview of computer hardware and other operating components suitable for implementing the invention, but is not intended to limit the applicable environments. It will be appreciated that the computer system 440 is one example of many possible computer systems which have different architectures. A typical computer system will usually include at least a processor, memory, and a bus coupling the memory to the processor. One of skill in the art will immediately appreciate that the invention can be practiced with other computer system configurations, including multiprocessor systems, minicomputers, mainframe computers, and the like. The invention can also be practiced in distributed computing environments where tasks are performed by remote processing devices that are linked through a communications network.

What is claimed is:

1. An apparatus for displaying three-dimensional medical images of a subject comprising:

means for storing three-dimensional voxel data representing a three-dimensional image of the subject with voxel values corresponding to a physical property of the subject;

means for defining a plurality of object parameter-sets from object parameters for a plurality of objects in the three-dimensional image, each object parameter specifying a spatial region, opacity and color of a corresponding object;

means for storing the plurality of object parameter-sets, each object parameter-set specifying a view of the three-dimensional image;

means for creating a plurality of view data of the three-dimensional image by applying the plurality of object parameter-sets to the voxel values;

means for creating a plurality of views of the three-dimensional image by applying projection-process parameters to the plurality of view data; and means for displaying the plurality of views of the three-dimensional image on an image display unit.

2. The apparatus of claim 1, wherein the means to display a plurality of views comprises:

means for displaying the plurality of views of the three-dimensional image in a plurality of display areas on the image display unit.

3. The apparatus of claim 2, wherein the three-dimensional voxel data comprises multiple sets of three-dimensional voxel data.

4. The apparatus of claim 3, wherein each of the multiple sets of the three-dimensional voxel data is acquired at a different time.

5. The apparatus of claim 3, wherein each of the multiple sets of the three-dimensional voxel data is acquired by a different modality.

6. The apparatus of claim 1 further comprising:

means for defining the object parameters for the plurality of objects in the three-dimensional image.

7. The apparatus of claim 1 further comprising:

means for defining the projection-process parameters.

8. A method for displaying three-dimensional medical images of a subject comprising:

obtaining three-dimensional voxel data representing a three-dimensional image of the subject with voxel values corresponding to a physical property of the subject;

obtaining a plurality of object parameter-sets from object parameters for a plurality of objects in the three-dimensional image, each object parameter specifying a spatial region, opacity and color of a corresponding object;

storing the plurality of object parameter-sets, each object parameter-set specifying a view of the three-dimensional image;

applying the plurality of object parameter-sets to the voxel values to create a plurality of view data of the three-dimensional image; and creating a plurality of views of the three-dimensional image by applying projection-process parameters to the plurality of view data.

9. The method of claim 8 further comprising:

displaying the plurality of views of the three-dimensional image on an image display unit.

10. The method of claim 9 wherein the each of the plurality of views is displayed in a separate display area on the image display unit.

11. The method of claim 8, wherein the three-dimensional voxel data comprises multiple sets of three-dimensional voxel data.

12. The method of claim 11, wherein each of the multiple sets of the three-dimensional voxel data is acquired at a different time.

13. The method of claim 11, wherein each of the multiple sets of the three-dimensional voxel data is acquired by a different modality.

14. The method of claim 8 further comprising:

obtaining the projection-process parameters.

15. A computer-readable medium having executable instructions for performing a method comprising:

obtaining three-dimensional voxel data representing a three-dimensional image of the subject with voxel values corresponding to a physical property of a subject;

obtaining a plurality of object parameter-sets from object parameters for a plurality of objects in the three-dimensional image, each object parameter specifying a spatial region, opacity and color of a corresponding object;

storing the plurality of object parameter-sets, each object parameter-set specifying a view of the three-dimensional image;

applying the plurality of object parameter-sets to the voxel values to create a plurality of view data of the three-dimensional image; and applying projection-process parameters to the plurality of view data to create a plurality of views of the three-dimensional image.

16. The computer-readable medium of claim 15 having further executable instructions comprising:
  displaying the plurality of views of the three-dimensional image on an image display unit.

17. A computer system comprising:
  a processor;
  a memory coupled to the processor through a bus; and
  an image process executed from the memory to cause the processor to store three-dimensional voxel data in the memory, to store a plurality of object parameter-sets in the memory, to create a plurality of view data from the plurality of object parameter-sets and the voxel values, and to create a plurality of views with a common viewpoint for a three-dimensional image from the plurality of view data.

18. The computer system of claim 17 further comprising an image display unit coupled to the processor through the bus and wherein the image process further causes the processor to display the plurality of views on the image display unit.

19. The computer system of claim 17, wherein the image process further causes the processor to retrieve a stored object parameter-set from memory to create one of the plurality of view data.

20. The computer system of claim 17 further comprising a computer-readable medium coupled to the processor through the bus and wherein the image process further causes the processor to store one of the plurality of object parameter-sets on the computer-readable medium.

21. The computer system of claim 20, wherein the image process further causes the processor to retrieve the stored object parameter-set from the computer-readable medium to create one of the plurality of view data.

* * * * *